United States Patent
Belongia

(10) Patent No.: US 8,821,171 B2
(45) Date of Patent: Sep. 2, 2014

(54) ROTATABLE PLUG ASSEMBLY AND HOUSING FOR A VOLATILE MATERIAL DISPENSER

(75) Inventor: David C. Belongia, Burlington, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 84 days.

(21) Appl. No.: 13/240,104

(22) Filed: Sep. 22, 2011

(65) Prior Publication Data

US 2013/0078834 A1    Mar. 28, 2013

(51) Int. Cl.
  *H01R 29/00* (2006.01)
  *A61L 9/03* (2006.01)
  *A01M 1/20* (2006.01)

(52) U.S. Cl.
  CPC .............. *A61L 9/037* (2013.01); *A01M 1/2077* (2013.01)
  USPC .......................................................... 439/166

(58) Field of Classification Search
  CPC .... H01R 27/00; H01R 2103/00; H01R 11/12; H01R 11/24; H01R 31/06
  USPC ................................... 439/166; 392/392–395
  See application file for complete search history.

(56) References Cited

U.S. PATENT DOCUMENTS

| | | |
|---|---|---|
| 1,613,647 A | 1/1927 | Davies et al. |
| 2,027,447 A | 1/1936 | Percy |
| 2,542,609 A | 2/1951 | Wyglendowski |
| 2,577,794 A | 12/1951 | Minard |
| 3,474,376 A | 10/1969 | Preiss |
| 4,084,079 A | 4/1978 | Costello |
| 4,458,228 A | 7/1984 | Baumgartner |
| 4,785,240 A | 11/1988 | Newell et al. |
| 4,927,376 A | 5/1990 | Dickie |
| 5,136,684 A | 8/1992 | Lonker et al. |
| 5,522,008 A | 5/1996 | Bernard |
| 5,556,192 A | 9/1996 | Wang |
| 5,567,181 A | 10/1996 | Lentz et al. |
| 5,574,821 A | 11/1996 | Babasade |
| 5,577,156 A | 11/1996 | Costello |
| 5,595,503 A | 1/1997 | Pittman et al. |
| 5,647,053 A | 7/1997 | Schroeder |
| 6,085,026 A | 7/2000 | Hammons et al. |

(Continued)

FOREIGN PATENT DOCUMENTS

| | | |
|---|---|---|
| EP | 0362397 A1 | 4/1990 |
| EP | 0696457 A1 | 2/1996 |

(Continued)

OTHER PUBLICATIONS

PCT/US2012/056254 International Search Report and Written Opinion dated Apr. 15, 2013.

*Primary Examiner* — Amy Cohen Johnson
*Assistant Examiner* — Vladimir Imas

(57) ABSTRACT

A rotatable electrical plug assembly for a volatile material dispenser includes a support block including a base having a base member and a wall extending from the base member and forming a cavity with the base member. The plug assembly further includes a cover disposed within the cavity and electrical plug pins extending through apertures in the base and including contacts that extend at an angle of about 90 degrees with respect to the plug pins, wherein the contacts are disposed between the base member and the cover. A ratio of an overall plug assembly thickness over a plug pin thickness is less than about 1.5.

14 Claims, 10 Drawing Sheets

(56) References Cited

U.S. PATENT DOCUMENTS

| | | | |
|---|---|---|---|
| 6,089,924 A | 7/2000 | Wang | |
| 6,328,581 B1 * | 12/2001 | Lee et al. | 439/106 |
| 6,402,352 B1 | 6/2002 | Summerford et al. | |
| 6,768,865 B2 | 7/2004 | Stathakis et al. | |
| 6,810,204 B2 | 10/2004 | Grone et al. | |
| 6,821,134 B2 * | 11/2004 | Chen | 439/131 |
| 6,839,506 B2 | 1/2005 | He et al. | |
| 6,862,403 B2 * | 3/2005 | Pedrotti et al. | 392/395 |
| 6,917,754 B2 * | 7/2005 | Pedrotti et al. | 392/395 |
| 6,950,607 B2 * | 9/2005 | Yip et al. | 392/395 |
| 6,966,799 B1 | 11/2005 | Wang | |
| 7,009,519 B2 | 3/2006 | Leonard et al. | |
| 7,052,281 B1 | 5/2006 | Meyberg et al. | |
| 7,063,558 B1 | 6/2006 | Chen | |
| 7,118,399 B1 * | 10/2006 | Wen et al. | 439/166 |
| 7,168,969 B1 * | 1/2007 | Wang | 439/173 |
| 7,375,282 B2 | 5/2008 | James | |
| 7,381,059 B2 * | 6/2008 | Wong | 439/22 |
| 7,439,709 B2 | 10/2008 | Bumiller | 320/114 |
| 7,462,074 B1 * | 12/2008 | Devlin et al. | 439/640 |
| 7,547,219 B2 * | 6/2009 | Zhuge | 439/173 |
| 7,575,436 B1 * | 8/2009 | Devlin et al. | 439/21 |
| 7,665,997 B1 | 2/2010 | Lin | |
| 7,688,030 B2 * | 3/2010 | Bumiller | 320/114 |
| 7,840,123 B2 * | 11/2010 | Belongia et al. | 392/392 |
| 7,914,292 B2 | 3/2011 | Honda | |
| 7,946,868 B1 * | 5/2011 | Chen | 439/173 |
| 8,033,847 B1 * | 10/2011 | Chen | 439/172 |
| 8,105,100 B1 * | 1/2012 | Cheng | 439/188 |
| 8,272,899 B2 * | 9/2012 | Youssefi-Shams et al. | 439/638 |
| 8,308,496 B2 * | 11/2012 | Youssefi-Shams et al. | 439/172 |
| 2003/0142817 A1 * | 7/2003 | Liao | 379/428.01 |
| 2003/0194225 A1 | 10/2003 | Pedrotti | |
| 2005/0218243 A1 * | 10/2005 | Zobele et al. | 239/34 |
| 2008/0315006 A1 * | 12/2008 | Belongia et al. | 239/44 |
| 2010/0285687 A1 | 11/2010 | Wadsworth | |
| 2011/0097914 A1 | 4/2011 | Lee | |

FOREIGN PATENT DOCUMENTS

| | | |
|---|---|---|
| EP | 1332765 A1 | 8/2003 |
| EP | 1714662 A1 | 10/2006 |
| WO | WO02/26274 A2 | 4/2002 |
| WO | WO03/013618 A1 | 2/2003 |
| WO | WO03/088430 A1 | 10/2003 |
| WO | WO2005/079874 A1 | 9/2005 |
| WO | WO2008/107366 A1 | 9/2008 |
| WO | WO2008/156805 A1 | 12/2008 |

* cited by examiner

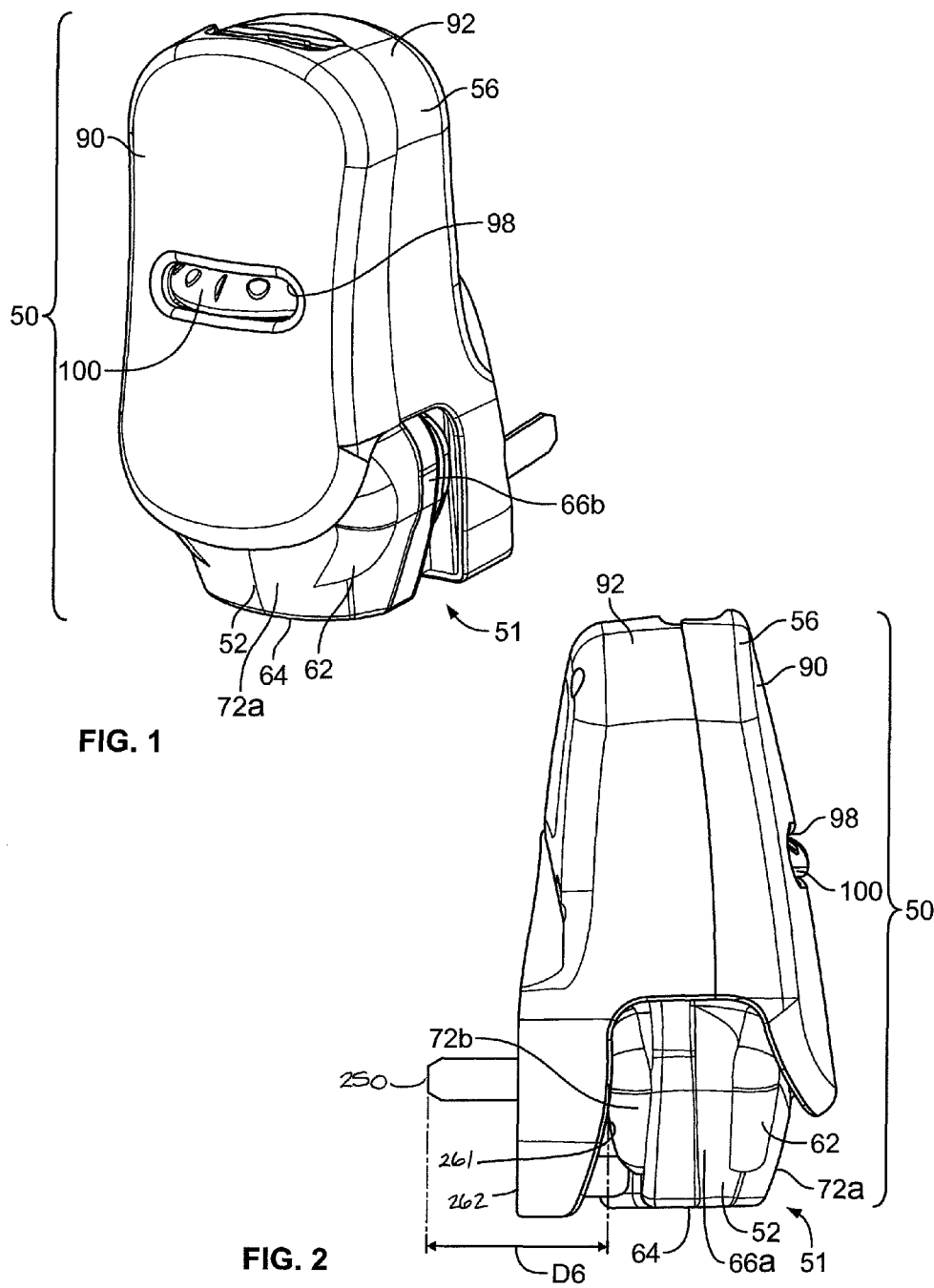

ROTATABLE PLUG ASSEMBLY AND HOUSING FOR A VOLATILE MATERIAL DISPENSER

CROSS REFERENCE TO RELATED APPLICATIONS

Not applicable.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates generally to a rotating electrical plug assembly and, more particularly, to a low profile rotating electrical plug assembly for use in a volatile material dispenser.

2. Description of the Background of the Invention

Various volatile material dispensers are known in the prior art and generally include a housing with a refill inserted therein. The refill generally includes a container for holding a volatile material therein. In some dispensers, the volatile material is passively emitted therefrom. In other dispensers, a diffusion element is utilized to facilitate the dispensing of the volatile material. Examples of diffusion elements include heaters, piezoelectric elements, fans, aerosol actuators, and the like. Regardless of the manner in which the volatile material is emitted, once the volatile material has been expended from the refill, the refill is removed by a user and replaced with a new refill.

One type of volatile material dispenser, referred to herein as a plug-in scented oil dispenser, includes a housing and a heater disposed within the housing. A refill for use with a plug-in scented oil dispenser generally includes a container with a volatile material therein and a wick in contact with the volatile material and extending out of the refill. Upon insertion of the refill into the dispenser, at least a portion of the wick is disposed adjacent the heater such that volatile material that moves through the wick is volatilized by the heater. The volatile material dispenser typically includes a plug assembly having electrical prongs extending outwardly from the housing. The electrical prongs are inserted into a standard electrical outlet and thereafter supply electrical energy to the volatile material dispenser. Plug-in scented oil dispensers may also utilize a fan to aid in vaporizing and dispersing volatile material.

One of the disadvantages of many of the volatile material dispensers and refills therefore, such as the plug-in scented oil dispenser discussed above, is that the plug assembly and electrical prongs are oriented in such a way so as to be compatible with only a single orientation of the volatile material dispenser with respect to the electrical outlet. For example, the vertical orientation of the electrical prongs with respect to the volatile material dispenser only allows a user of the volatile material dispenser to insert the dispenser in an upright manner into a vertically oriented electrical outlet. The user must rotate the volatile material dispenser in a horizontal manner to insert the volatile material dispenser into a horizontally oriented electrical outlet. Rotation of the dispenser in this manner is undesirable for numerous reasons including, at least, that the volatile material may leak from the dispenser and/or be removed from contact with the wick if the dispenser is disposed in a horizontal position.

A solution has been attempted to try to remedy the aforementioned problems in the form of a rotating plug assembly, which allows the rotation of the electrical prongs on the plug assembly from a vertically oriented position to a horizontally oriented position. The user may then adjust the plug assembly based on the desired orientation, which allows the volatile material dispenser to remain upright, while still receiving electrical energy. However, a further problem is created by the continued rotation of the plug assembly of the present devices utilizing such an assembly. Specifically, strain is created on various portions of the plug assembly during rotation, which causes the plug assembly parts to fatigue over time. The fatigue may lead to loosen wires in the plug assembly that could create unstable connection points between the plug assembly and the wires and render the volatile material dispenser inoperable.

Another disadvantage of many volatile material dispensers, especially those with rotating plug assemblies, is that the mechanical features necessary to allow for rotation of the plug assembly adds bulk in the form of a thicker dispenser. In particular, dispensers with rotating plug assemblies (and even those without) tend to stand a distance off the wall, thereby drawing attention to the dispenser and simply getting in the way. Consumers generally desire dispensers that are compact and unnoticeable, and thus, manufacturers of volatile material dispensers are constantly looking for ways to design smaller volatile material dispensers without sacrificing the quality of the dispenser.

SUMMARY

According to one aspect of the present invention, a rotatable electrical plug assembly for a volatile material dispenser includes a support block including a base having a base member and a wall extending from the base member and forming a cavity with the base member. The plug assembly further includes a cover disposed within the cavity and electrical plug pins extending through apertures in the base and including contacts that extend at an angle of about 90 degrees with respect to the plug pins, wherein the contacts are disposed between the base member and the cover. A ratio of an overall plug assembly thickness over a plug pin thickness is less than about 1.5.

In a different aspect of the present invention, a rotatable electrical plug assembly includes a support block including a base having a base member and a cylindrical wall extending from the base member and forming a cavity with the base member. The plug assembly further includes a cover disposed within the cavity and electrical plug pins extending through apertures in the base and including contacts that extend at an angle of about 90 degrees with respect to the plug pins. The contacts are retained within continuous projections formed in the base member by an interference or friction fit.

In a further aspect of the present invention, a housing for a volatile material dispenser includes a front face and a rear face forming a chamber therebetween for receipt of a container. The housing further includes an electrical plug assembly rotatably retained within an opening in the rear face, wherein the plug assembly includes a support block and electrical pins extending from the support block. A ratio of an overall plug assembly thickness over a plug pin thickness is less than about 1.5.

BRIEF DESCRIPTION OF THE DRAWINGS

FIG. 1 is a top, front isometric view of a volatile material dispenser having a container disposed within a housing of the dispenser;

FIG. 2 is a side elevational view of the dispenser of FIG. 1;

Other aspects and advantages of the present invention will become apparent upon consideration of the following detailed description, wherein similar structures have like or similar reference numerals.

DETAILED DESCRIPTION

The present invention is directed to an electrical plug assembly for a volatile material dispenser. While the present invention may be embodied in many different forms, several specific embodiments are discussed herein with the understanding that the present invention is to be considered only as an exemplification of the principles of the invention, and it is not intended to limit the invention to the embodiments illustrated.

Figure 3:
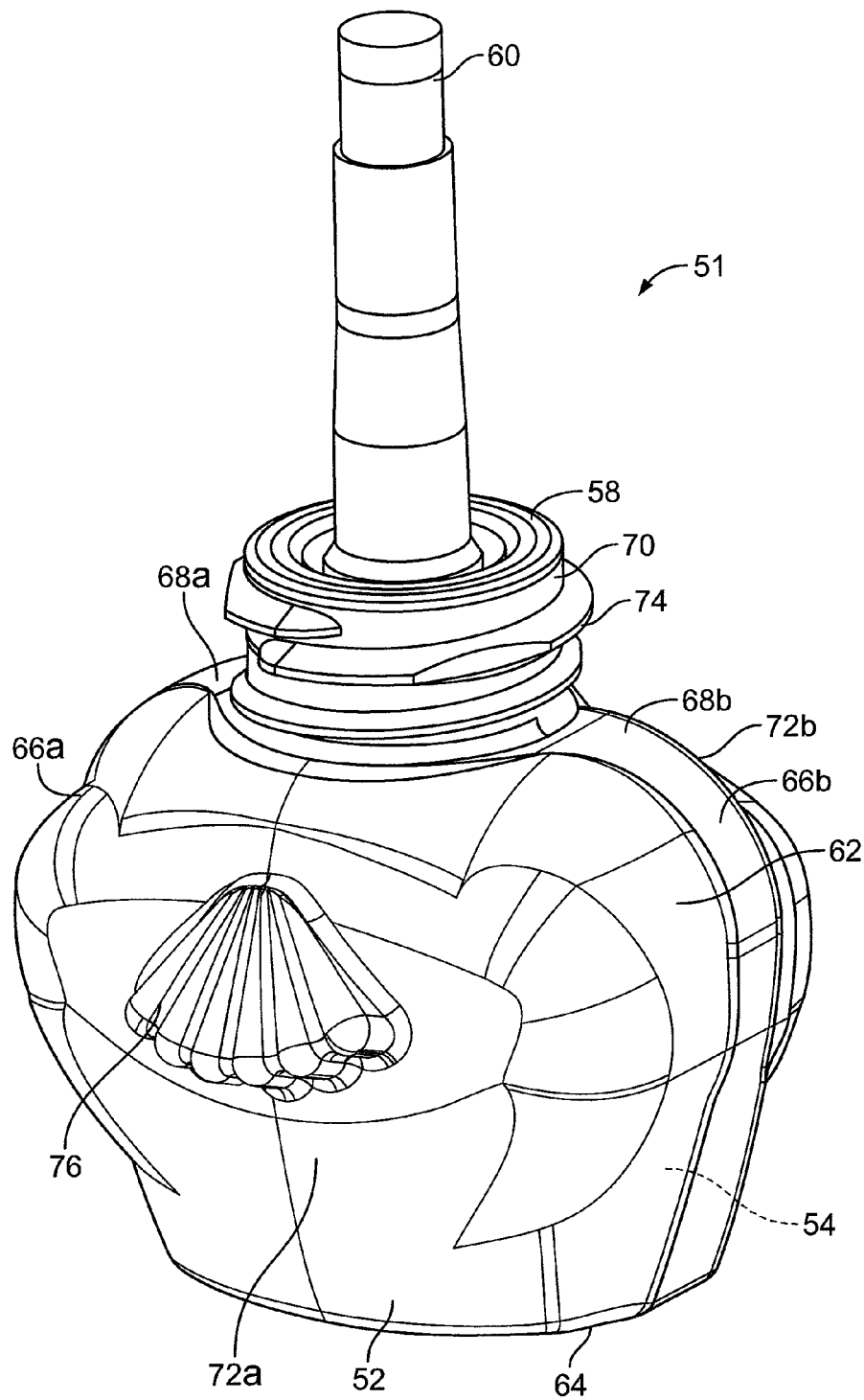
FIG. 3 is a top, front isometric view of the container of FIG. 1.

Referring to the drawings, FIG. 1 depicts a volatile material dispenser 50 having a refill 51 including a container 52 with a volatile material 54 therein, wherein the container 52 is adapted to be retained by a housing 56. As best seen in FIG. 3, the container 52 includes a retaining mechanism 58 to hold a wick 60 within the container 52. The container 52 includes a body 62 with the volatile material 54 disposed therein. The body 62 includes a base portion 64 and first and second opposing sidewalls 66a, 66b that extend upwardly and outwardly prior to curving inwardly toward first and second top walls 68a, 68b, respectively. The first and second top walls 68a, 68b are integral with a neck 70. Similarly, third and fourth opposing front and rear walls 72a, 72b, respectively, curve upwardly toward the neck 70.

The neck 70 includes a threaded portion 74 disposed on an outer surface thereof and an opening (not shown) disposed through a top portion thereof, wherein the opening allows access to the volatile material 54. The container 52 further optionally includes raised portions 76 extending outwardly from one or more of the third and fourth opposing front and rear walls 72a, 72b. In one embodiment, the raised portions 76 are in the form of inverted shell-shaped members. Although a specific dispenser 50 and container 52 are described with particularity, it is contemplated that any type of electrical dispenser and any type of container may be used with the electrical plug assembly described herein. For example, dispensers useful for the present invention include, but are not limited to, the dispensers described in Belongia et al. U.S. Pat. No. 7,840,123, Varanasi et al. U.S. Pat. No. 6,968,124, Beland et al. U.S. Patent Application Publication No. 2011/0049259, Zobele U.S. Patent Application Publication No. 2005/0180736, and Pedrotti et al. U.S. Patent Application Publication No. 2003/0194225. Further, containers useful for the present invention include, but are not limited to, the containers described in U.S. Pat. No. 7,032,831, and the containers described in U.S. patent application Ser. No. 12/969,261, filed on Dec. 15, 2010, both of which are owned by the same assignee as the present invention.

The volatile material 54 disposed in the container 52 may be any type of volatile material adapted to be dispensed into an environment. For example, the container 52 may include a cleaner, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof. Additives may be included in the volatile material, such as, for example, fragrances and/or preservatives.

Figure 4:
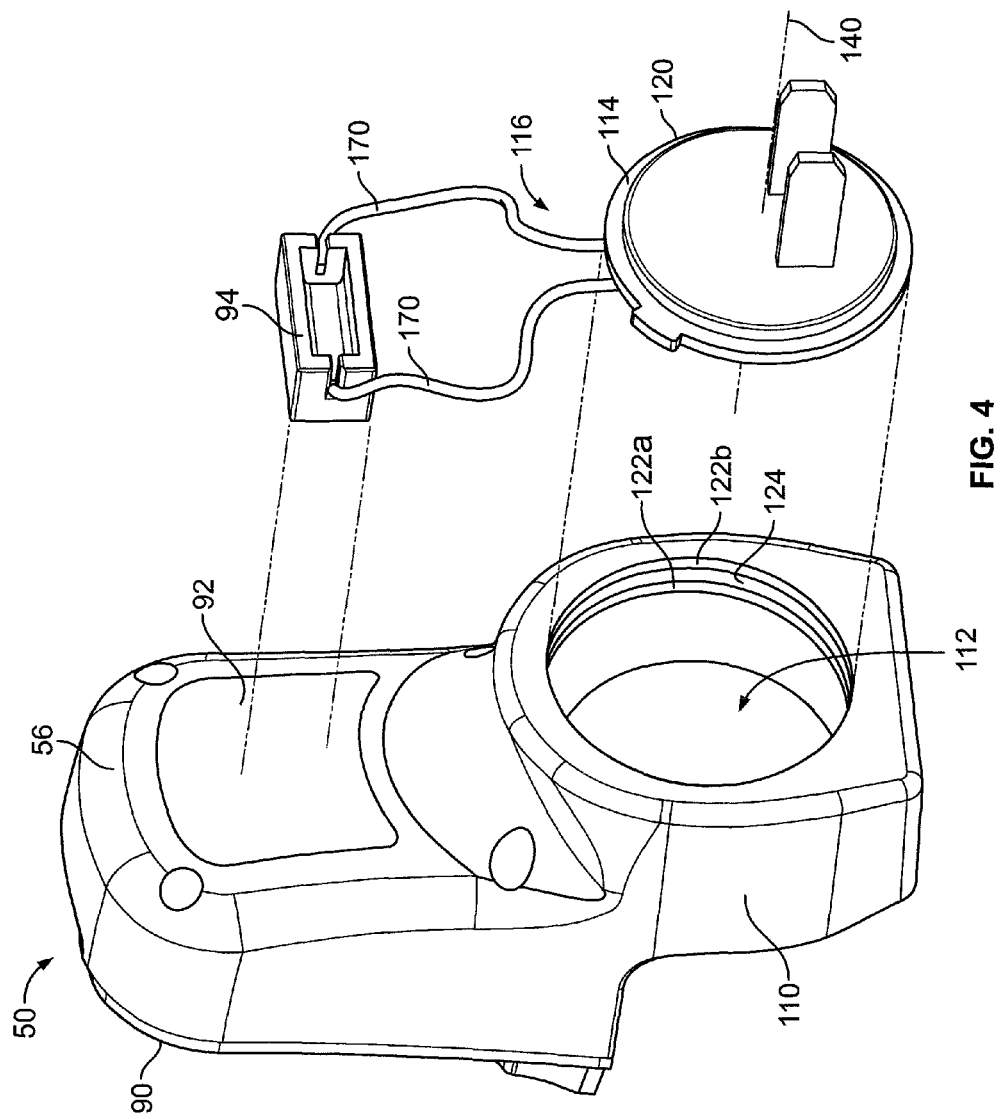
FIG. 4 is an exploded rear isometric view of the housing of FIG. 1 with an electrical plug assembly and heater removed therefrom.
Figure 5:
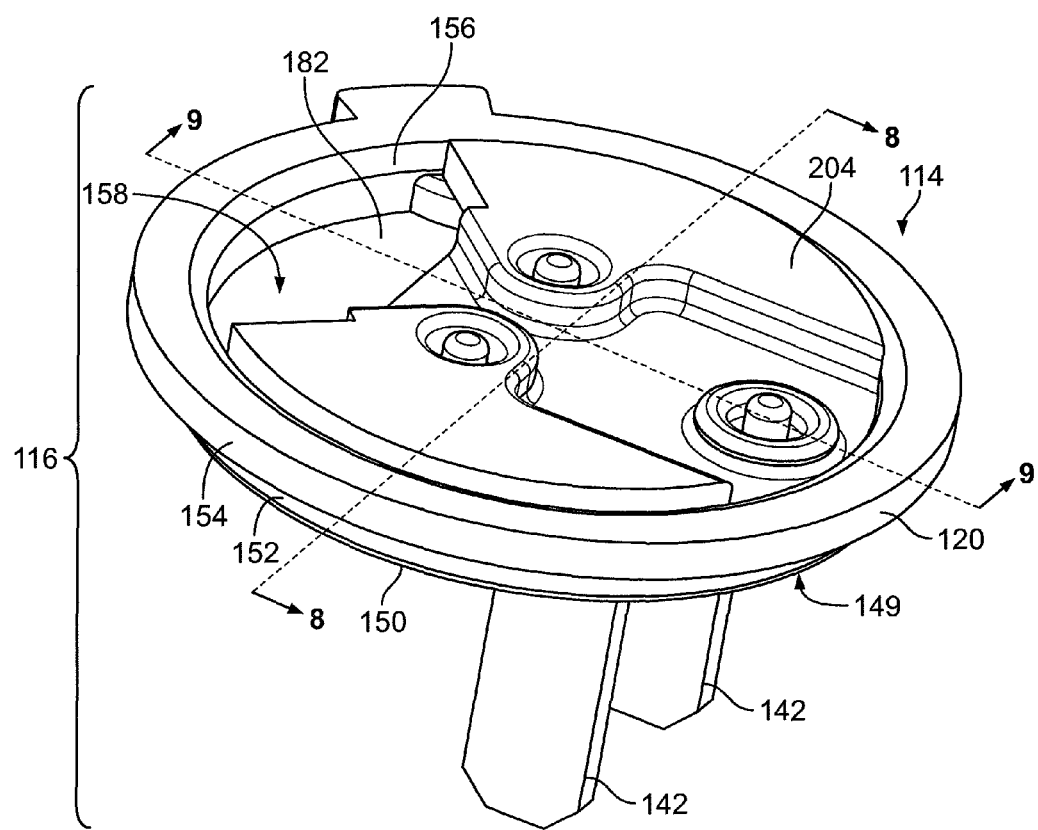
FIG. 5 is an enlarged top isometric view of the electrical plug assembly depicted in FIG. 4.

Now turning generally to FIGS. 1, 2, and 4, the housing 56 of the volatile material dispenser 50 includes a slightly curved front face 90 attached to a curvilinear rear face 92 to form a chamber (not shown) therebetween. The container 52 is inserted into the housing 56 by inserting the wick 60 thereof upwardly into the chamber. The container 52 is retained within the housing 56 by conventionally known means, including a snap-fit connection, a threaded interaction, and the like. Preferably, a portion of the wick 60 is disposed adjacent a heater 94 (see FIG. 4) that is disposed in the housing 56. The front face 90 of the housing 56 optionally includes an opening 98 with a control mechanism 100 extending partially therethough, which in the present embodiment comprises a rotatable dial adapted to control operational parameters of the volatile material dispenser 50.

As best seen in FIGS. 2 and 4, the rear face 92 of the housing 56 includes a lower end 110 having a circular opening 112 (FIG. 4) adapted to receive a support block 114 that provides a base for an electrical plug assembly 116. Although not shown, a stop assembly or other mechanism to allow rotation through about 90 degrees is disposed on an internal sidewall 118 defining the opening 112 and an outer perimeter 120 of the support block 114. The stop assembly or other mechanism may be any type known in the art, for example, one of those shown in copending Belongia et al. U.S. application Ser. No. 13/096,767 or Pedrotti et al. U.S. Patent Application Publication No. 2003/0194225. Two continuous projections 122a, 122b extend inwardly from the sidewall 118 defining the opening 112. During assembly of the dispenser 50, the outer perimeter 120 of the support block 114 is snapped into a channel 124 formed between the projections 122a, 122b to fixedly retain the support block 114 within the dispenser 50. Optionally, any other structure of method known in the art may be utilized for fixedly retaining the support block 114 within the dispenser 50.

When the container 52 is inserted into the housing 56 (see FIG. 1), the top of the wick 60 extends upwardly through the chamber such that a portion of the wick 60 is disposed adjacent the heater 94 (FIG. 4). The container 52 is releasably retained within the housing 56 by conventionally known manners. The positioning of the wick 60 with respect to the heater 94 (FIG. 4) enables the heat generated by the heater or heating element to assist in vaporizing the volatile material 54 drawn up through the wick 60 and to thereby release the volatile material into the surrounding atmosphere.

Figure 6:
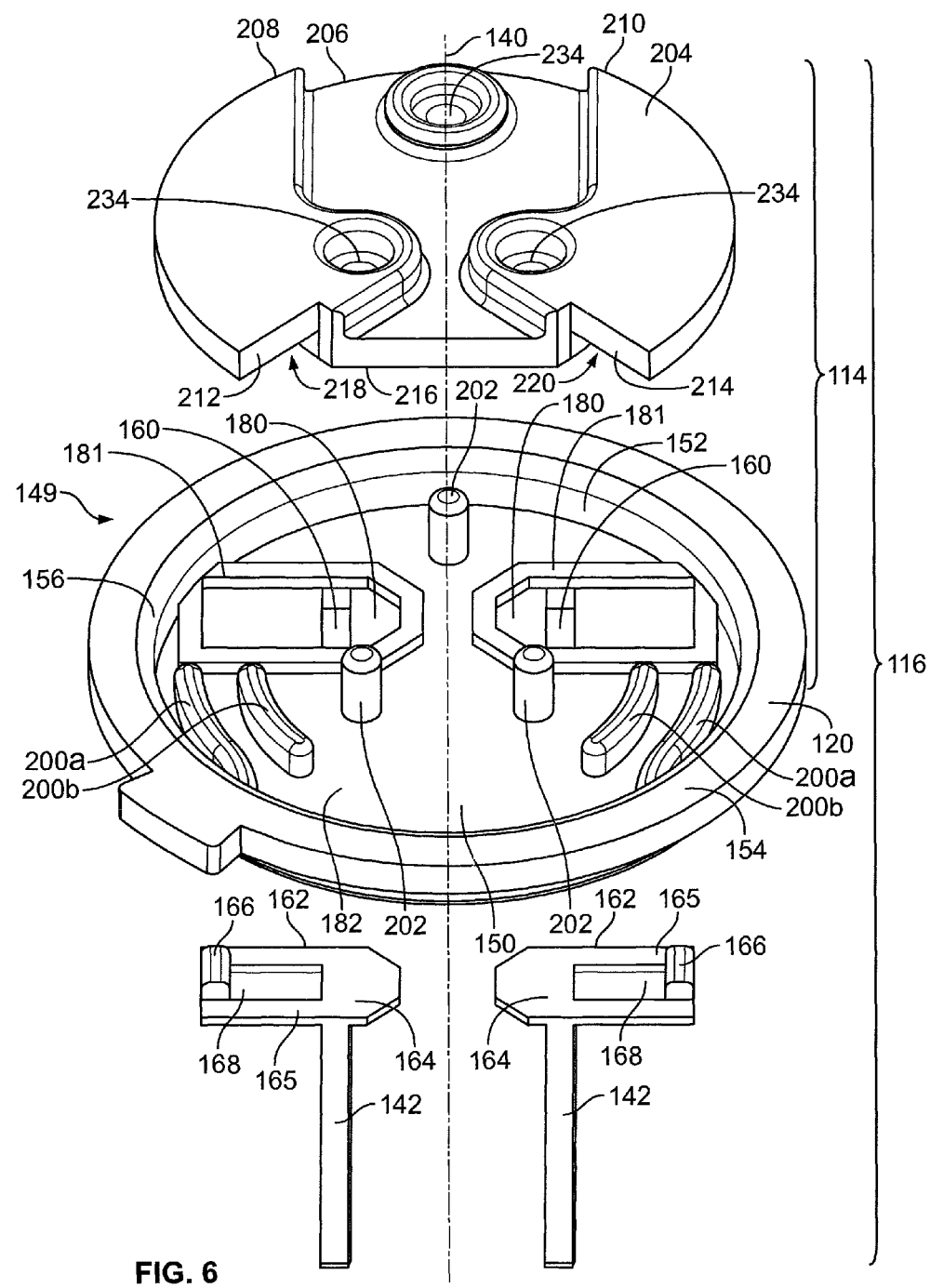
FIG. 6 is an enlarged top isometric view of the electrical plug assembly of FIG. 4 with a cover and plug pins removed therefrom.
Figure 7:
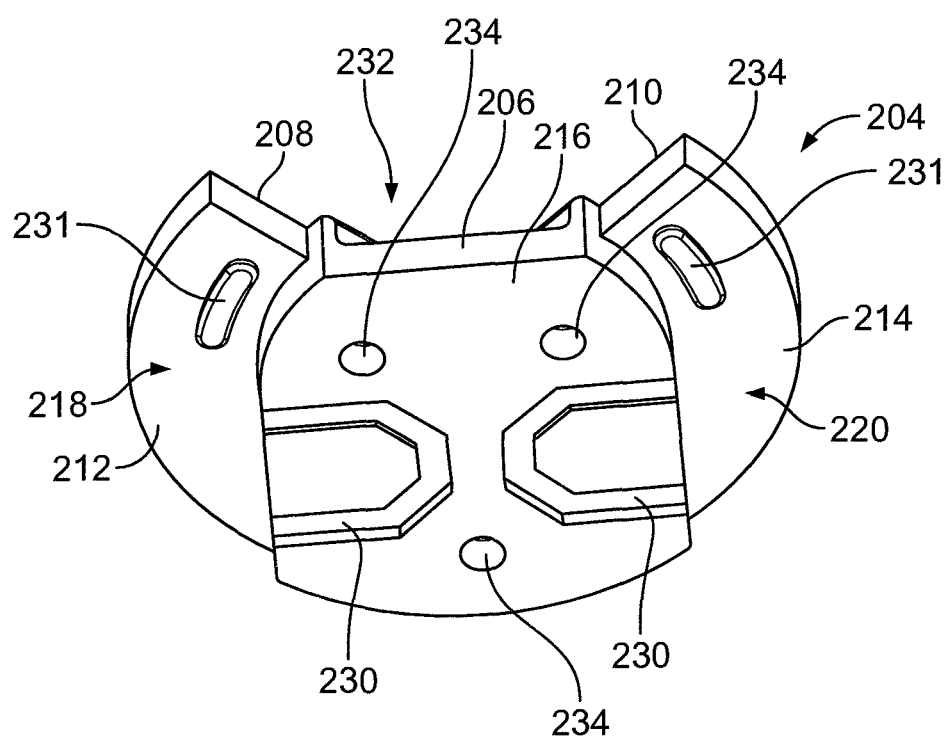
FIG. 7 is a bottom isometric view of the cover of FIG. 6.
Figure 8:
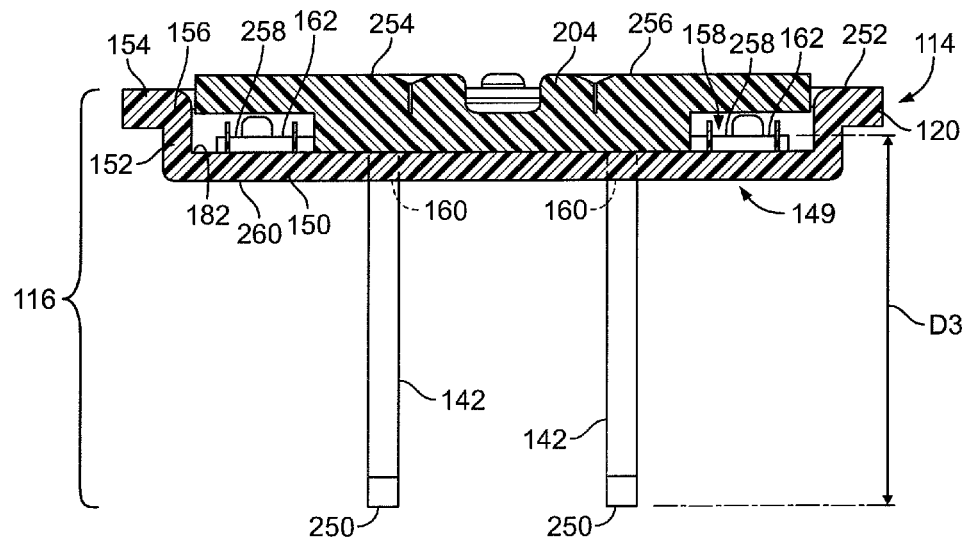
FIG. 8 is a cross-sectional view of the electrical plug assembly of FIG. 4 taken generally along the lines 8-8 of FIG. 5.

Referring to FIGS. 4-9, the support block 114 can be rotated approximately 90 degrees around a longitudinal axis 140 (FIG. 4) of the plug assembly 116 parallel to electrical plug pins 142. The rotational capability of the support block 114 enables the volatile material dispenser 50 to be plugged into any conventional electrical outlet (either with outlet openings that are parallel to the ground or perpendicular to the ground) so that the wick 60 is approximately perpendicular to the ground. As best seen in FIGS. 5, 6, 8, and 9, the support block 114 includes a base 149 having a circular base member 150, a cylindrical sidewall 152 extending outwardly from the base member 150, and an annular flange 154 extending outwardly from a top edge 156 of the cylindrical sidewall 152. The base member 150 and the cylindrical sidewall 152 form a shallow cavity 158. As seen in FIG. 8, the base 149 further includes a set of apertures 160 extending through the base member 150. The plug pins 142 are metallic for conducting electricity and further include generally flat contacts 162 connected to the plug pins at first ends 164 thereof and extending at about a 90 degree angle with respect to the plug pins 142. Second ends 165 of the plug pins 142 include terminals 166 and openings 168 adjacent the terminals 168 for bonding, soldering, or otherwise connecting wires 170 thereto, to conduct electricity from the electrical outlet, through the plug pins 142 and wires 170, to one or more electrical components of the dispenser 50. When the plug assembly 116 is assembled, the contacts 162 extending from the plug pins 142 are disposed within similarly shaped grooves 180 formed by an upstanding wall 181 extending from the base member 150. A slight interference or friction fit is maintained between the contacts 162 and the grooves 180 to prevent movement of the contacts 162 in a plane formed by an upper surface 182 the base member 150. Although two wires 170 are depicted, any suitable number of wires may be utilized.

Referring to FIG. 6, the support block 114 may include one or more guide posts or rails 200 extending outwardly from the base member 150. In particular, as will be discussed in greater detail hereinafter, the guide rails 200a, 200b act to position the wires such that rotation of the plug assembly 116 minimizes mechanical strain on the wires 170, thereby minimizing damage to the wires 170 and loss of electrical current through the dispenser 50. Still further, as will be discussed in greater detail hereinafter, one or more projections 202 may extend outwardly from the base member 150 to aid in securing a generally circular cover 204 to the base 149.

The cover 204, as best seen in FIGS. 6 and 7, includes a first generally planar inner wall 206 and second and third generally planar outer walls 208, 210 extending outwardly from opposite sides of the first wall 206. Bottom surfaces 212, 214 of the first and second walls 208, 210, respectively, form a plane that is spaced along the longitudinal axis 140 of the plug assembly 116 from a plane formed by a bottom surface 216 of the first wall 206. The difference in the planes creates cutouts 218, 220 below the bottom surfaces 212, 214 and adjacent the first wall 206. Referring to FIG. 7, the bottom surface 216 of the first wall 206 includes grooves 230 that have a shape that is the same as the upstanding walls 181 extending from the base member 150. Similarly, the walls 208, 210 include guide rails 231 having a shape that is the same as the guide rails 200b. The cover 204 further includes a cutout 232 (FIG. 7) of about 90 degrees, which will be discussed in greater detail hereinafter.

Figure 9:
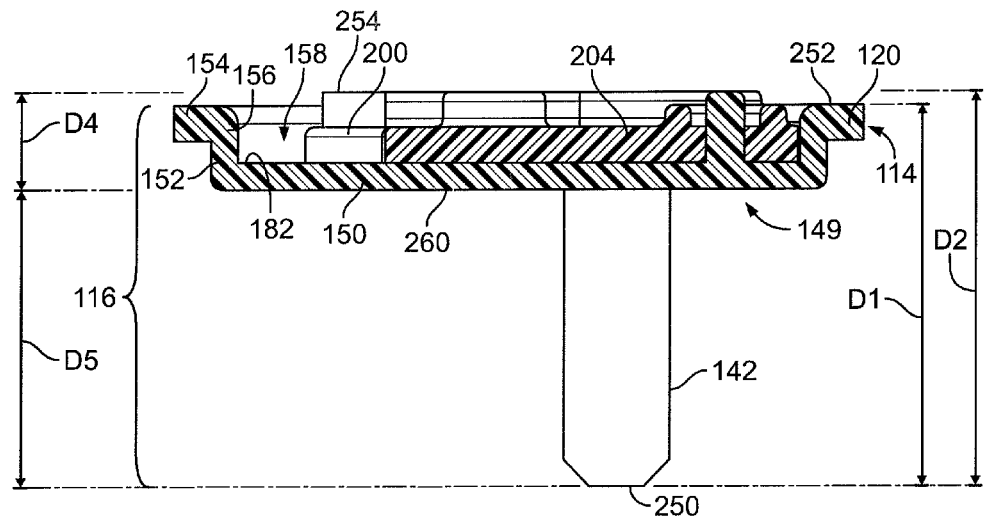
FIG. 9 is a cross-sectional view of the electrical plug assembly of FIG. 4 taken generally along the lines 9-9 of FIG. 5.

Referring to FIGS. 2, 8, and 9, the plug assembly 116 of the present invention enables the construction of a smaller, more compact dispenser 50. In particular, as seen in FIGS. 8 and 9, the plug assembly 116 has a dimension D1 between an end 250 of the plug pins 142 and an outer surface 252 of the annular flange 154 of less than or equal to about 0.87 inches (22 mm) and a dimension D2 (overall plug assembly 116 thickness, including any connections to wires 170) between the end 250 of the plug pins 142 and outer surfaces 254, 256 of the planar outer walls 208, 210, respectively, of less than or equal to about 0.91 inches (23 mm). In addition, a dimension D3 (overall plug pin 142 thickness) between the end of the plug pins 142 and an outer surface 258 of the contacts 162 is less than or equal to about 0.75 inches (19 mm). A dimension D4 (overall support block 114 thickness) represents a distance between the outer surfaces 254, 256 of the planar outer walls 208, 210, respectively, and an outer surface 260 of the base member 150, which is between about 0.20 inch (5 mm) and about 0.24 inch (6 mm). Still further, a dimension D5 (a plug pin 142 thickness) represents a distance between the end 250 of the plug pins 142 and the outer surface of the base member 260. D5 is conventional per country and is about 0.6 inches (15.5 mm) in the United States. As seen in FIG. 2, a dimension D6, which is an overall dispenser 50 and plug assembly 116 thickness, is about 1.05 inch (26.7 mm). The dimension D6 represents a dimension between the ends 250 of the plug pins 142 and an outwardly facing wall 261 of the dispenser 50 that encloses the plug assembly 116 and which is opposite a rear wall 262 of the housing 56. In addition, a dimension of the dispenser 50 between the rear wall 262 of the housing 56 and the outwardly facing wall 261 (i.e., the dimension D6 minus the plug pins 142) can be as small as 0.375 inches (9.5 mm).

In one embodiment, the plug assembly 116 and volatile material dispenser 50 are dimensioned such that a plug assembly ratio D2/D5 is less than about 1.5. In another embodiment, the plug assembly ratio D2/D5 is less than about 1.3. In one embodiment, the plug assembly 116 and the volatile material dispenser 50 are dimensioned such that a dispenser/plug assembly ratio D6/D5 is less than about 1.9. In another embodiment, the dispenser/plug assembly ratio D6/D5 is less than about 1.75. And in yet another embodiment, the dispenser/plug assembly ratio D6/D5 is less than about 1.6. Although the dimension D5 representing the thickness of the plug pin may be different in other countries or areas of the world, the plug assembly and dispenser/plug assembly ratios would generally be the same for differently dimensioned plug pins.

The plug assemblies 116 as disclosed herein are universal in nature in that the plug assemblies 116 are dimensioned to fit within multiple volatile material dispensers having different housings, different diffusion elements, different refills, etc. In particular, a volatile material dispenser need only have an opening dimensioned to accept a plug assembly 116 disclosed herein, other features necessary for proper operation of the plug assembly 116, and about 0.375 inch (9.5 mm) of internal clearance between the opening and the outwardly facing wall 261 or any component other component of the dispenser 50 (e.g., diffusion element, refill, etc.) within the dispenser (the internal clearance being the same as the dimension D6 minus the plug pins 142). This internal clearance need only be large enough to allow routing of wires from the plug assembly 116 and allow rotation of the plug assembly 116.

Figure 10:
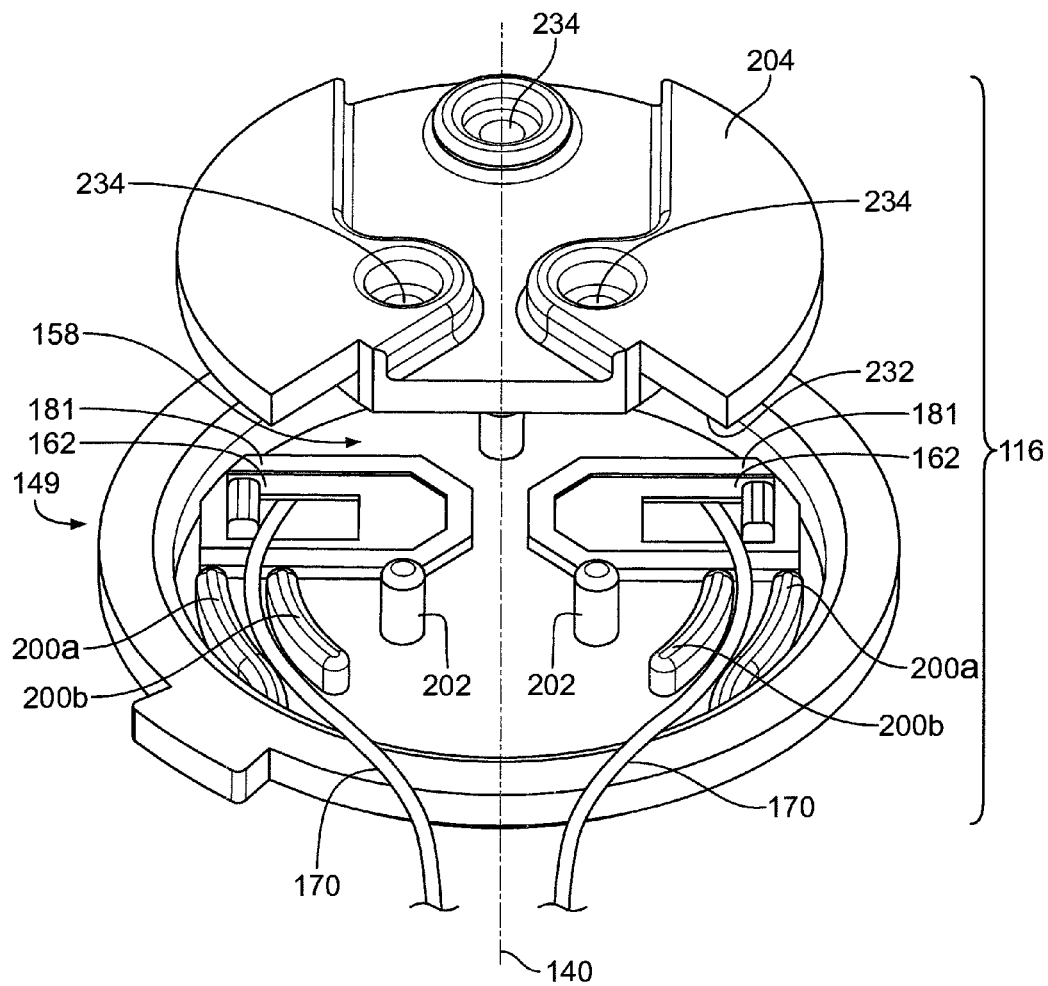
FIG. 10 is an enlarged top isometric view of the electrical plug assembly of FIG. 4 with a cover removed therefrom and wires connected to and extending from the plug assembly.
Figure 11:
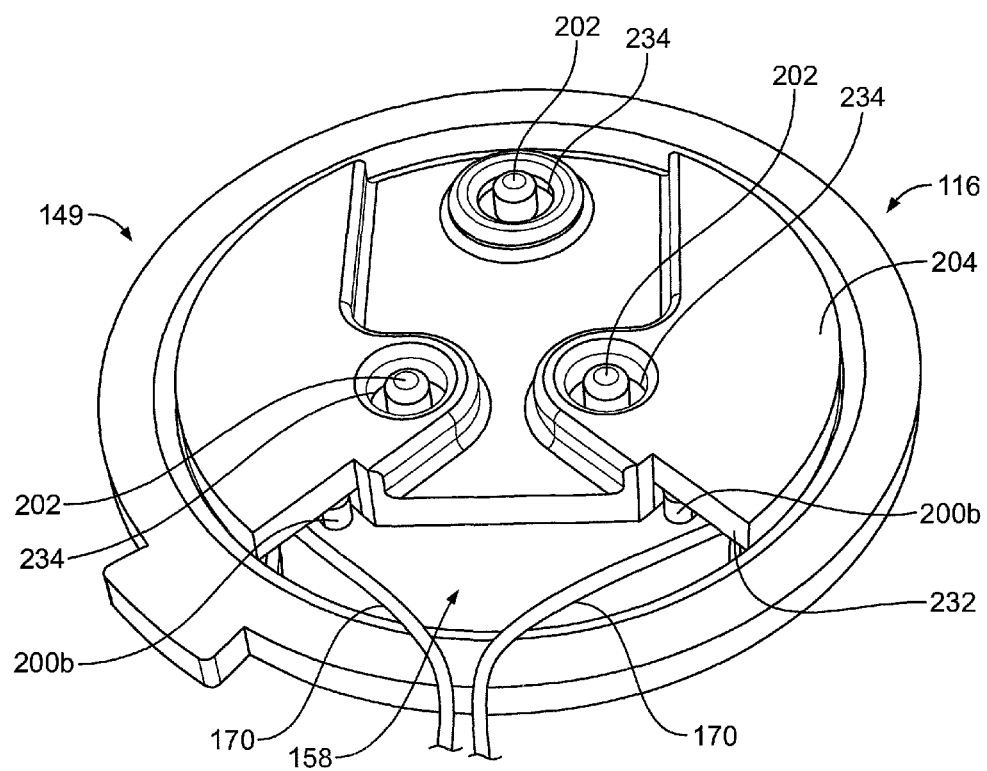
FIG. 11 is an enlarged top isometric view of the electrical plug assembly of FIG. 4 with wires connected to and extending therefrom.

As seen in FIGS. 10 and 11, the plug assembly 116 is assembled by first inserting the plug pins 142 through the apertures 160 (not shown) and thereafter, the wires 170 are connected to the contacts 162 in a convention manner (or the wires 170 are connected and the plug pins 142 are inserted through the apertures 160) and the wires 170 are routed between the guide rails 200a, 200b (if present). Once the wires 170 are positioned, the cover 204 is inserted within the cavity 158 formed in the base 149 and the projections 202 are heat staked or otherwise secured within circular apertures 234 formed within the cover 204. When the cover 204 and base 149 are joined, the upstanding walls 181 extending from the base member 150 are disposed within the similarly shaped grooves 300 (FIG. 7), thereby sandwiching the contacts 162 therebetween and preventing movement of the contacts along the longitudinal axis 140 (as well as within a plane perpendicular to the longitudinal axis 140). The guide rails 231 (FIG. 7) also abut the guide rails 200b to retain the wires 170 in position. When the cover 204 is disposed within the base 149, the wires 170 are routed between the guide rails 200a, 200b, 231 and out the cutout 232. Optionally, if one or more of the guide rails 231 is omitted, the wires 170 are simply routed toward and out the cutout 232. Routing the wires 172 in a direction perpendicular to the longitudinal axis 140 of the plug assembly 116 before routing them parallel to the longitudinal axis 140 minimizes mechanical strain placed on the wires 170 during rotation of the plug assembly 116, as will be discussed in greater detail hereinafter.

Referring to FIGS. 10 and 11, routing the wires 170 parallel to the base member 150 before routing the wires 170 perpendicular to the base member 150 and out the plug assembly 116 diffuses the rotation forces caused by rotating the plug assembly 116 into the cover 204 of the assembly 116. In conventional plug assemblies, ends 205 of the wires 170 are crimped or attached to terminals that extend outwardly and are parallel or coincident with the plug pins and rotational forces are exerted on the ends 205 of the wires 170 at the terminals, thereby creating strain, an unstable point for the wires, and a potential break in the wires. In the plug assembly 116, any mechanical strain on the wires 170 is diffused or transferred to the point where the wires 170 exit the cover 204 (at the cutout 232) due to the confinement of the wires 170 between the base 149 and the cover 204.

Figure 12:
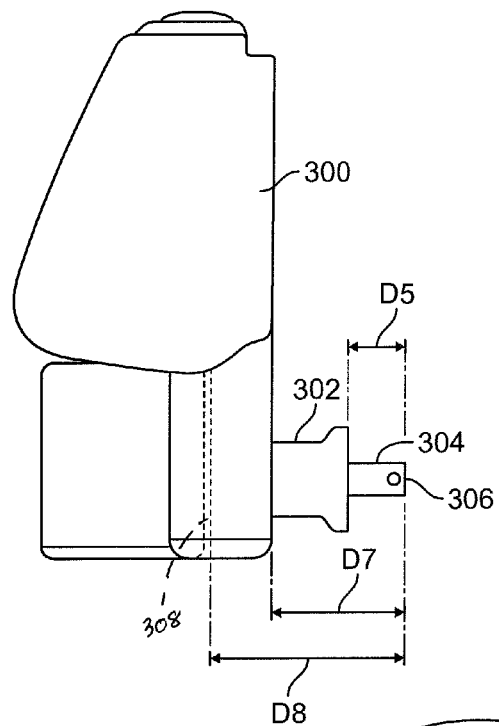
FIGS. 12-14 are side elevational views of currently available commercial dispensers.
Figure 13:
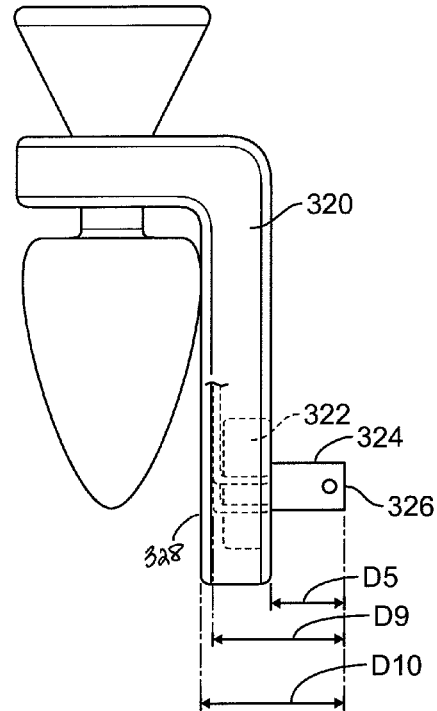
Figure 14:
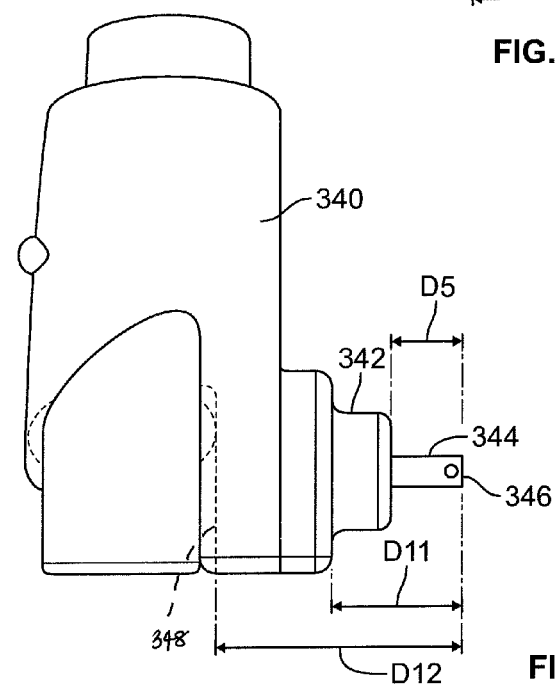

FIGS. 12-14 depict commercially available dispensers. In particular, FIG. 12 is a commercial dispenser sold by Reckitt Benckiser under Air Wick® Scented Oils. The Air Wick® dispenser includes a housing 300 with a rotating plug assembly 302 having plug pins 304 extending therefrom. A plug pin 304 thickness (D5) is conventional and the same for the Air Wick® dispenser as for other dispensers. An overall plug assembly 302 thickness D7 for the Air Wick® dispenser is about 1.2 inch (30 mm) and a dimension D8, which is an overall dispenser and plug assembly thickness, is about 1.6 inch (40 mm). In particular, the dimension D8 represents a dimension between ends 306 of the plug pins 304 and an outwardly facing wall 308 of the housing 300. Therefore, a plug assembly ratio D7/D5 is about 1.94 and a dispenser/plug assembly ratio D8/D5 is about 2.58.

The dispenser of FIG. 13 is a commercial dispenser sold by Bath and Body Works, Inc. under Wallflowers® Pluggable Home Fragrance. The Bath and Body dispenser includes a housing 320 with a rotating plug assembly 322 having plug pins 324 extending therefrom. A plug pin 324 thickness (D5) is conventional and the same for the Bath and Body dispenser as for other dispensers in the United States. An overall plug assembly 322 thickness D9 for the Bath and Body dispenser is about 1.14 inch (29 mm) and a dimension D10, which is an overall dispenser and plug assembly thickness, is about 1.34 inch (34 mm). In particular, the dimension D10 represents a dimension between ends 326 of the plug pins 324 and an outwardly facing wall 328 of the housing 320. Therefore a plug assembly ratio D9/D5 is about 1.87 and a dispenser/plug assembly ratio D10/D5 is about 2.19.

The dispenser of FIG. 14 is a commercial dispenser sold by S.C. Johnson & Son, Inc. under Glade® PlugIns® Scented Oil. The Glade® dispenser includes a housing 340 with a rotating plug assembly 342 having plug pins 344 extending therefrom. A plug pin 344 thickness (D5) is conventional and the same as for other dispensers in the United States. An overall plug assembly 342 thickness D11 for the Glade® dispenser is about 1.02 inch (26 mm) and a dimension D12, which is an overall dispenser and plug assembly thickness, is about 1.65 inch (42 mm). In particular, the dimension D12 represents a dimension between ends 346 of the plug pins 344 and an outwardly facing wall 348 of the housing 340. Therefore, a plug assembly ratio D11/D5 is about 1.68 and a dispenser/plug assembly ratio D12/D5 is about 2.71.

Although the plug assemblies herein are described as being utilized with dispensers that utilize refills with plug-in scented oils, the plug assemblies may be utilized for any electrical dispenser from which any type of volatile material is dispensed out of any type of refill. In particular, the plug assemblies may be utilized with dispensers having one or more of a heater, a fan, a piezoelectric element, and/or other components disposed in a housing thereof to help facilitate the release of volatile material. Any of the aforementioned components may be electrically connected to the plug assemblies in manners described herein or known in the art.

The dispensers may further include one or more openings in the housing to allow for the volatile material to be dispensed from the housing to the surrounding environment. The housing may include a variety of internal implements to help secure the various refills disclosed herein, such as, for example, snaps, ridges, undercuts, lips, notches, and/or other attachment methods. The dispensers may optionally include one or more refills and may operate using a variety of timing sequences as known in the art.

Any of the embodiments described herein may be modified to include any of the structures or methodologies disclosed in connection with other embodiments.

Further, although directional terminology, such as front, back, upper, lower, etc. may be used throughout the present specification, it should be understood that such terms are not limiting and are only utilized herein to convey the orientation of different elements with respect to one another.

All documents cited in the Detailed Description of the Invention are, in relevant part, incorporated herein by reference; the citation of any document is not to be construed as an admission that it is prior art with respect to the present invention.

INDUSTRIAL APPLICABILITY

The present invention provides volatile material dispensers having a rotating electrical plug assembly. The plug assemblies include a base, a cover, and a set of plug pins extending out the base and disposed between the base and the cover. Wires are routed between the base and the cover to decrease mechanical strain on the wires. The base, the cover, and the plug pins are also dimensioned to provide a lower profile dispenser.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A rotatable electrical plug assembly for a volatile material dispenser, the assembly comprising:
   a support block including a base having a base member and a wall extending from the base member and forming a cavity with the base member;
   a cover disposed within the cavity;
   electrical plug pins extending through apertures in the base and including contacts that extend at an angle of about 90 degrees with respect to the plug pins, wherein the contacts are disposed between the base member and the cover;
   at least one wire connected to one of the contacts; and
   at set of rails extending from the base member and positioned to guide the wire between the rails and between the base member and the cover.

2. The rotatable plug assembly of claim 1, wherein a ratio of an overall plug assembly thickness over a plug pin thickness is less than about 1.3.

3. The rotatable plug assembly of claim 1, wherein a ratio of a dimension between the plug pins and an outwardly facing wall of the dispenser over the plug pin thickness (dispenser/plug assembly ratio) is less than about 1.9.

4. The rotatable plug assembly of claim 3, wherein the dispenser/plug assembly ratio is less than about 1.75.

5. The rotatable plug assembly of claim 4, wherein the dispenser/plug assembly is less than about 1.6.

6. The rotatable plug assembly of claim 3, wherein the dispenser component is a wall, other external surface, or a diffusion element.

7. The rotatable plug assembly of claim 1, wherein the at least one wire runs perpendicular to the plug pins before running parallel to the plug pins and out a cutout in the cover to reduce mechanical strain in the wire during rotation of the plug assembly.

8. The rotatable plug assembly of claim 7, wherein the wires are sandwiched between the cover and the base.

9. The rotatable plug assembly of claim 1, wherein the support block further includes an annular flange extending outwardly from the cylindrical wall, the annular flange adapted to rotatably fit within a channel formed within an opening within the dispenser.

10. The rotatable plug assembly of claim 1 that can be interchangeably used with two or more volatile material dispensers.

11. A rotatable electrical plug assembly, comprising:
    a support block including a base having a base member and a cylindrical wall extending from the base member and forming a cavity with the base member;
    a cover disposed within the cavity; and
    electrical plug pins extending through apertures in the base and including contacts that extend at an angle of about 90 degrees with respect to the plug pins, wherein the contacts are retained by an interference or friction fit created by walls extending from the base member, wherein the walls form cavities that have shapes complimentary to the contacts and wherein the cover includes grooves with shapes that are complementary to shapes of the walls and, when the cover is disposed over the base member, at least a portion of each of the walls fit within the respective grooves such that an area of the cover inside the grooves aids in securing the contacts in place.

12. The rotatable plug assembly of claim 11, wherein a ratio of an overall plug assembly thickness over a plug pin thickness is less than about 1.5.

13. The rotatable plug assembly of claim 12, wherein the rotation of the overall plug assembly thickness over the plug pin thickness is less than about 1.3.

14. The rotatable plug assembly of claim 12, wherein a ratio of a dimension between the plug pins and an outwardly facing wall of a dispenser in which the plug assembly is disposed over the plug pin thickness (dispenser/plug assembly ratio) is less than about 1.9.

* * * * *